(12) United States Patent
Gan et al.

(10) Patent No.: US 7,169,576 B2
(45) Date of Patent: Jan. 30, 2007

(54) METHOD FOR IDENTIFYING DRUG METABOLITES WITH DANSYLATED GLUTATHIONE

(75) Inventors: Jinping Gan, Princeton, NJ (US); Timothy W. Harper, Morrisville, PA (US); William G. Humphreys, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 32 days.

(21) Appl. No.: 11/031,292

(22) Filed: Jan. 7, 2005

(65) Prior Publication Data

US 2005/0186651 A1    Aug. 25, 2005

Related U.S. Application Data

(60) Provisional application No. 60/534,870, filed on Jan. 8, 2004.

(51) Int. Cl.
*C12Q 1/26* (2006.01)

(52) U.S. Cl. .......................................... 435/25; 530/335

(58) Field of Classification Search ...................... None
See application file for complete search history.

(56) References Cited

U.S. PATENT DOCUMENTS

| 6,830,897 B2 * | 12/2004 | Avery et al. ................... 435/15 |
| 6,995,022 B1 * | 2/2006 | van Breemen et al. ...... 436/150 |
| 2005/0287623 A1 * | 12/2005 | Yan et al. ...................... 435/25 |

OTHER PUBLICATIONS

Soglia et al. (Jul. 2, 2004) J Pharma Biomed Anal 36, 105-116.*
Yan et al. (2004) Anal Chem 76, 6835-6847.*
Chen, W.G. et al., "Reactive Metabolite Screen for Reducing Candidate Attrition in Drug Discovery", Adv. Exp. Med. Biol., vol. 500, pp. 521-524 (2001).
Gardner, I. et al., "A Comparison of the Oxidation of Clozapine and Olanzapine to Reactive Metabolites and the Toxicity of these Metabolites to Human Leukocytes", Molecular Pharmacology, vol. 53, pp. 991-998 (1998).
Graham, D.J. et al., "Troglitazone-Induced Liver Failure: A Case Study", The American Journal of Medicine, vol. 114, pp. 299-306 (2003).
Hammermeister, D.E. et al., "Characterization of dansylated glutathione, glutathione disulfide, cysteine and cystine by narrow bore liquid chromatography/electrospray ionization mass spectrometry", Rapid Communications in Mass Spectrometry, vol. 14, pp. 503-508 (2000).

Iverson, S. et al., "Predicting drug-induced agranulocytosis: characterizing neutrophil-generated metabolites of a model compound, DMP 406, and assessing the relevance of an in vitro apoptosis assay for identifying drugs that may cause agranulocytosis", Chemico-Biological Interactions, vol. 142, pp. 175-199 (2002).
Jones, D.P. et al., "Glutathione measurement in human plasma: Evaluation of sample collection, storage and derivatization conditions for analysis of dansyl derivatives by HPLC", Clinica Chimica Acta, vol. 275, pp. 175-184 (1998).
Kassahun, K. et al., "Studies on the Metabolism of Troglitazone to Reactive Intermediates in Vitro and in Vivo. Evidence for Novel Biotransformation Pathways Involving Quinone Methide Formation and Thiazolidinedione Ring Scission", Chem. Res. Toxicol., vol. 14, No. 1, pp. 62-70 (2001).
Khojasteh-Bakht, S.C. et al., "Metabolism of (R)-(+)-pulegone and (R)-(+)-menthofuran by Human Liver Cytochrome P-450s: Evidence for Formation of a Furan Epoxide", Drug Metabolism and Disposition, vol. 27, No. 5, pp. 574-580 (1999).
Li, A.P. et al., "A review of the common properties of drugs with idiosyncratic hepatotoxicity and the 'multiple determinant hypothesis' for the manifestation of idiosyncratic drug toxicity", Chemico-Biological Interactions, vol. 142, pp. 7-23 (2002).
Maggs, J.L. et al., "The Metabolic Formation of Reactive Intermediates from Clozapine, a Drug Associated with Agranulocytosis in Man", The Journal of Pharmacology and Experimental Therapeutics, vol. 275, No. 3, pp. 1463-1475 (1995).
Nelson, S.D., "Mechanisms of the Formation and Disposition of Reactive Metabolites That Can Cause Acute Liver Injury", Drug Metabolism Reviews, vol. 27, Nos. 1 & 2, pp. 147-177 (1995).
Park, B.K. et al., "Advances in molecular toxicology—towards understanding idiosyncratic drug toxicity", Toxicology, vol. 153, pp. 39-60 (2000).
Park, B.K. et al., "Metabolic activation in drug allergies", Toxicology, vol. 158, pp. 11-23 (2001).
Smith, M.T., "Mechanisms of Troglitazone Hepatotoxicity", Chemical Research in Toxicology, vol. 16, No. 6, pp. 679-687 (2003).
Tettey, J.N. et al., "Enzyme-Induction Dependent Bioactivation of Troglitazone and Troglitazone Quinone In Vivo", Chem. Res. Toxicol., vol. 14, No. 8, pp. 965-974 (2001).
Uetrecht, J.P., "New Concepts in Immunology Relevant to Idiosyncratic Drug Reactions: The 'Danger Hypothesis' and Innate Immune System", Chemical Research in Toxicology, vol. 12, No. 5, pp. 387-395 (1999).

* cited by examiner

*Primary Examiner*—Ralph Gitomer
(74) *Attorney, Agent, or Firm*—Sammy G. Duncan, Jr.

(57) ABSTRACT

The present application relates to a sensitive and quantitative method using dansylated glutathione as a trapping agent for the detection of reactive metabolites in the field of drug discovery. The fluorescent tag attached to the dansylated glutathione does not impede the ability of glutathione to react with reactive metabolites.

2 Claims, No Drawings

METHOD FOR IDENTIFYING DRUG METABOLITES WITH DANSYLATED GLUTATHIONE

RELATED APPLICATION

This application claims priority benefit under Title 35 § 119(e) of U.S. Provisional Application No. 60/534,870, filed Jan. 8, 2004, the contents of which are herein incorporated by reference.

TECHNICAL FIELD

The present application relates to a sensitive and quantitative method employing a fluorescently labeled trapping agent for the detection of reactive metabolites. One common mode of drug-induced toxicity is the formation of reactive, electrophilic metabolites. Thiol-containing nucleophiles can be used as trapping agents for a wide variety of electrophilic metabolites that are generated from incubations of test compounds with in vitro enzymatic systems. When the thiol-containing nucleophiles are tagged with a fluorescent label, then the formation of trapped electrophilic species can be quantitatively determined. This quantitative assay of thiol adduct formation will be especially useful in the lead optimization phase of drug discovery.

BACKGROUND OF THE INVENTION

The preclinical prediction of adverse reactions of a drug candidate is a difficult and elusive task. This is primarily attributed to the lack of scientific understanding of the mechanism of some adverse reactions and also to the lack of animal models. The prediction is especially difficult in the case of idiosyncratic drug reactions, which have very low frequency of occurrence, no apparent dose-response relationship, and no animal models for evaluation. (Uetrecht, J. P., *Chem Res Toxicol,* 1999, 12(5), 387–95; Park, B. K., et al, *Toxicology,* 2000, 153(1–3), 39–60; and Li, A. P., *Chem Biol Interact,* 2002, 142(1–2), 7–23). At present, there is not a commonly accepted experimental approach to predict idiosyncratic drug reactions.

Most of the drugs that are associated with idiosyncratic drug reactions form reactive metabolites that react with endogenous nucleophiles, including proteins (Li 2002). Two hypotheses have been proposed that link reactive metabolites with idiosyncratic reactions, namely the hapten hypothesis and the danger hypothesis, both involve the triggering of immune response following the insult from reactive metabolites. (Uetrecht 1999; Park, Kitteringham et al. 2000; and Park, B. K., Naisbitt, D. J. et al., *Toxicology,* 2001, 158(1–2), 11–23). In either case, it seems logical to screen for reactive metabolites preclinically to reduce the risk of such drug reactions and to decrease the attrition rate of new drug candidates.

Thiol-containing nucleophiles have long been used for the trapping of reactive intermediates. Glutathione is the most important physiological thiol containing nucleophile. Glutathione is a tripeptide γ-glu-cys-gly produced endogenously. It is an important cellular component that is crucial for the cellular homeostasis of redox potential and a natural defense against oxidative stress. Glutathione is also regarded primarily as a detoxification agent because it reacts with many known reactive metabolites and the resulting glutathione adducts are usually nontoxic and excreted readily from the human body. Because of its ability to react with a variety of reactive metabolites, glutathione has been widely used as a in vitro trapping agent for the characterization and mechanistic study of reactive metabolites. There are several approaches that have been reported for the preclinical detection and screening for glutathione adduct formations, namely, neutral loss LC-MS/MS screening and tritiated glutathione trapping. Neutral loss LC-MS/MS screening utilizes the characteristic fragmentation pattern of glutathione and glutathione adducts when they are subjected to the collision induced decomposition (CID) in the second quadrapole of a triple quadrapole mass spectrometer (Chen, W. G. et al., *Adv Exp Med Biol,* 2001, 500, 521–4). This method is rapid and relatively sensitive, however it is not quantitative. The other method utilizes radiolabeled glutathione (tritiated) and adducts can be quantitatively determined by radioactivity counting. Technical and financial concerns have limited the use of the radiolabeled glutathione method. Adequate separation of the glutathione adducts from the unreacted material is challenging and results in insufficient sensitivity. Further, the use of radioactivity requires special facilities and creates environmentally hazardous waste material. Finally, the radiolabeled glutathione method is relatively expensive.

Thus, there exists a need for a sensitive, quantitative, and cost-effective method to trap reactive metabolites in vitro. The present application answers this need.

DETAILED DESCRIPTION OF THE INVENTION

Synthetic scheme of fluorescently tagged thiol containing trapping agents are outlined in Scheme 1. The synthesis is achieved by reacting fluorescent agents with thiol-containing molecules. The thiol group is protected by the formation of a disulfide bond. Subsequent reduction of the disulfide bond yields the proposed trapping agent with a free thiol group.

SCHEME 1

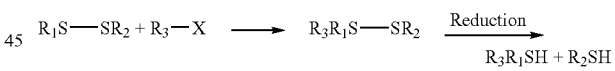

General Synthesis of Fluorescently Tagged Thiol-Containing Molecules $R_1SH$: the thiol-containing molecules; $R_2SH$: thiol-protecting group (can be $R_1SH$ itself); $R_3$—X: fluorescent derivatizing agent, in which $R_3$ is the fluorescence tag and X is a good leaving group.

The synthetic thiol-containing fluorescent trapping agent can be used to trap thiol-reactive intermediates that are generated from incubations of compounds of interest with any in vitro enzymatic bioactivation system. Any adduct produced from such incubations is separated by HPLC and monitored by both fluorescence detector and mass spectrometer. Peaks representing trapped intermediates are quantitated in the resulting fluorescence chromatogram, and the molecular identities of such peaks are characterized with the mass spectrometric information.

EXAMPLES

Example 1

Synthesis and Application of dGSH as a Fluorescent Trapping Agent

Dansyl chloride was used in the early days of protein chemistry to derivatize terminal amino acids. The current method utilizes the fluorescent nature of the dansyl group to derivatize glutathione at the free amino group of glutamyl moiety. Since thiol groups react with dansyl chloride as well, oxidized glutathione is used. After dansyl derivatization, dithiothreitol is used to reduce the disulfide bond yielding the final dansyl glutathione product. The identity of dGSH is confirmed by MS/MS fragmentation (FIG. 1). A slow HPLC gradient was developed to ensure enough separation of dGSH with potential dGSH trapped reactive metabolites. As shown in FIG. 2, dGSH is adequately separated from the oxidized dGSH (dGSH dimer) that was formed during the incubation. dGSH is used in a large excess (20 times more than substrate concentrations), and some background peaks clustered around the dGSH peak in the blank chromatogram. Thus chromatographic separation is very important for the detection and quantitation of dGSH adducts.

Materials

Dansyl chloride, oxidized glutathione, and NADPH were purchased from Sigma-Aldrich (Milwaukee, Wis.). Pooled human liver microsomes (HLM, Lot No. 16) were purchased from Gentest (Woburn, Mass.).

Synthesis of Dansyl Glutathione (dGSH)

The synthesis protocol was adapted from published methods (Jones, D. P., Carlson, J. L. et al., *Clin Chim Acta*, 1998, 275(2), 175–84; and Hammermeister, D. E., Serrano, J. et al., *Rapid Commun Mass Spectrom*, 2000, 14(6), 503–8) 0.15 g of oxidized glutathione was dissolved in 2 ml of water, and the pH was adjusted to 8.8 by the addition of tetraborate buffer solution (saturated sodium tetraborate in 1 N NaOH). The resulting solution was stirred in the dark at room temperature, and 0.27 g of dansyl chloride dissolved in 20 ml of acetone was added. An additional 5 ml of water was added to keep the oxidized glutathione in solution. The reaction was allowed to go overnight. The reaction mixture was extracted twice with chloroform (1:1). The aqueous layer was mixed with equal volume of 0.1 M Tris buffer (pH 8.0, with 1 mM EDTA), followed by the addition of 1 g of dithiothreitol to reduce the disulfide bond. The resulting dansyl glutathione solution was further purified by passing through a C 18 SPE column (Burdick & Jackson, Muskegon, Mich.).

In Vitro Incubation

A human liver microsome (Gentest, Woburn, Mass. Lot No. 16) incubation mixture containing 50 µM substrate, 1 mM dGSH, 1 mg/ml microsomes, and 100 mM potassium phosphate buffer (pH 7.4) was preincubated for 3 min. at 37° C. The reaction was initiated by the addition of 1 mM NADPH. The final incubation volume was 0.5 ml. Samples without substrate or dGSH were used as blank or control, respectively. The concentration of organic solvent (acetonitrile for most of the compounds) was kept under 1% in all incubations. After 30 min of incubation, the reaction was terminated by the addition of one volume of ice-cold acetonitrile. After vortexing and centrifugation, 40 µL of the resulting supernatant was analyzed by HPLC.

Instruments and Methods

A Shimadzu LC-10Avp HPLC system was used for separation. Aliquots of samples were injected onto a 4.6 mm×150 mm Phenomenex Prodigy C-18 column. The mobile phase contained 0.1% formic acid in water as solvent A and 0.1% formic acid in acetonitrile as solvent B. The analyses were performed using a mobile phase flow rate of 1 ml/min and an initial composition of 95% A:5% B. The mobile phase was hold at 95% A: 5% B for 3 min and then changed to 50% A: 50% B in 20 min, then to 5% A: 95% B in 10 min. The mobile phase was held at 5% A: 95% B for 2 min before dropping back to 95% A: 5% B in 1 min. The total analysis time is 36 min. A fluorescence detector (Shimadzu RFL-10A) was used for the detection and quantitation of adducts formed. The excitation and emission wavelength were set at 340 and 525 nm respectively. The HPLC eluent coming out of the fluorescence detector was connected to a Finnigan LCQ ion trap mass spectrometer. Full scans with mass range from m/z 300–1100 Da were obtained with alternating positive and negative ionization. Quantitation of dGSH trapped reactive metabolites was accomplished by comparison of peak area in the fluorescence chromatogram with that of dGSH as an external standard.

Results dGSH adducts were detected in incubations with drugs that are known to form reactive metabolites. As summarized in Table 1, five compounds that are known to generate reactive metabolites produced positive responses in the fluorescence trace.

TABLE 1

Dansyl GSH trapping of reactive intermediates with compounds known to cause idiosyncratic reactions or to form GSH adducts

| Compound | Structure | % of substrate trapped as dGSH adduct |
|---|---|---|
| R-(+)-Pulegone | 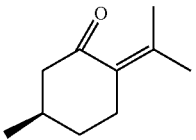 | 13 |

TABLE 1-continued
Dansyl GSH trapping of reactive intermediates with compounds known to cause idiosyncratic reactions or to form GSH adducts
| Compound | Structure | % of substrate trapped as dGSH adduct |
|---|---|---|
| Troglitazone | 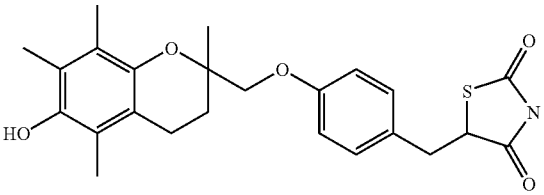 | 7.1 |
| Diclofenac | 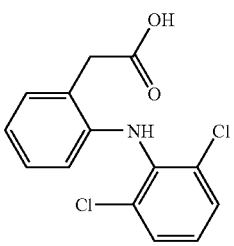 | 1.6 |
| Clozapine | 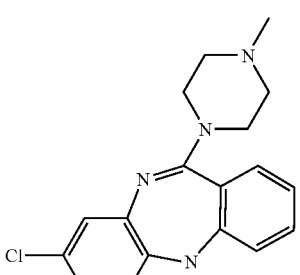 | 3.8 |
| Acetaminophen | 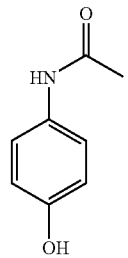 | 0.5 |

Example 1.1

Troglitazone

Troglitazone was associated with idiosyncratic liver toxicity and was subsequently withdrawn from the market. (Kassahun, K., Pearson, P. G. et al., *Chem Res Toxicol*, 2001, 14(1), 62–70; Tettey, J. N., Maggs, J. L. et al., *Chem Res Toxicol*, 2001, 14(8), 965–74; Graham, D. J., Green, L. et al., *Am J Med*, 2003, 114(4), 299–306; and Smith, M. T., *Chem Res Toxicol*, 2003, 16(6), 679–87). Consistent with literature reports regarding GSH adducts, the major peak has a mass of 779 amu and corresponds to the direct addition of dGSH to troglitazone.

Example 1.2

Clozapine

Clozapine is associated with increased incidences of agranulocytosis. (Maggs, J. L. et al., *J Pharmacol Exp Ther*, 1995, 275(3), 1463–75; Gardner, I. et al., *Mol Pharmacol*, 1998, 53(6), 991–8; and Iverson, S. et al., *Chem Biol Interact*, 2002, 142(1–2), 175–99) Two peaks were found in the chromatogram that had a mass of 833 amu, this is consistent with the literature regarding GSH adducts formed with clozapine.

Examples 1.3–1.5

R-(+)-Pulegone, Diclofenac and Acetaminophen

Peaks were found with R-(+)-pulegone (m/z 688 amu), diclofenac (m/z 815 amu) and acetaminophen (m/z 689amu) that have apparent masses consistent with a dGSH addition. (Nelson, S. D., *Drug Metab Rev*, 1995, 27(1–2), 147–77; and Khojasteh-Bakht, S. C., Chen, W. et al., *Drug Metab Dispos*, 1999, 27(5), 574–80).

Examples 1.6–1.10

Five widely prescribed drugs in the current US market that are not associated with any significant adverse events were tested in this system (Table 2). Lack of adduct formation was expected based on their safety profile and these studies served as method of further validation to test the level of false positives in this system. None of these drugs showed any signal of adduct formation.

TABLE 2 dGSH trapping result of 5 widely prescribed drugs that are not associated with any significant adverse events

| Drug | Structure | % of drug trapped as dGSH adduct |
|---|---|---|
| Omeprazole | 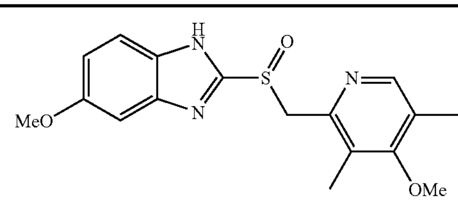 | n.d. |
| Atorvastatin | 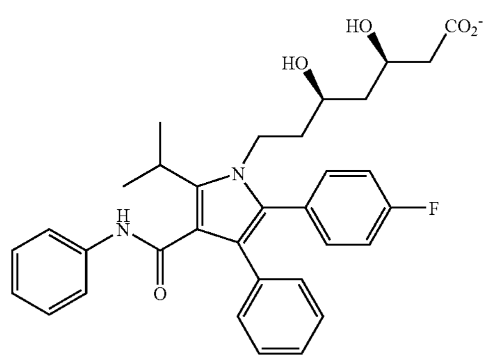 | n.d. |
| Celecoxib | 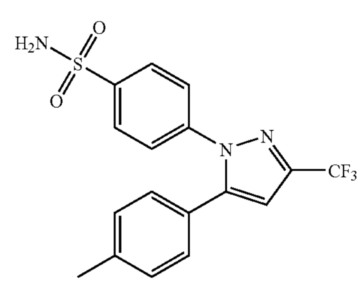 | n.d. |

TABLE 2-continued dGSH trapping result of 5 widely prescribed drugs that are not associated with any significant adverse events

| Drug | Structure | % of drug trapped as dGSH adduct |
|---|---|---|
| Fluoxetine | 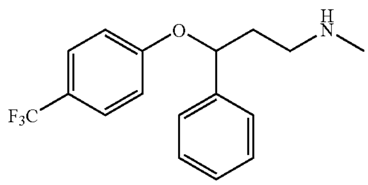 | n.d. |
| Loratadine | 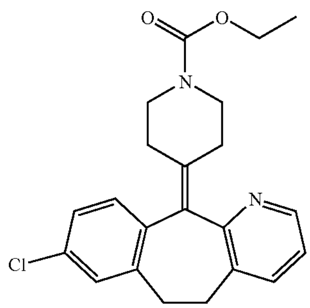 | n.d. |

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A method for identifying drug candidates that produce reactive metabolites, comprising:
    (a) incubating the drug candidate in vitro with a human liver microsome incubation mixture in the presence of dansylated glutathione;
    (b) detecting any drug candidate-dansylated glutathione adducts formed in step (a) through the use of a fluorescence detector having excitation and emission wavelength settings of 340 and 525 nm. respectively; and
    (c) identifying the drug candidate-dansylated glutathione adduct by mass spectrometry.

2. The method according to claim 1, further comprising:
    separating the drug candidate, dansylated glutathione and any drug candidate-dansylated glutathione adduct formed in the incubating step.

* * * * *